United States Patent
Ferret et al.

(10) Patent No.: US 7,691,412 B2
(45) Date of Patent: Apr. 6, 2010

(54) PROLONGED RELEASE BIODEGRADABLE MICROSPHERES AND METHOD FOR PREPARING SAME

(75) Inventors: Eulalia Ferret, El Prat De Llobregat (ES); Miguel Angel Asin, Cerdanyola Del Valles (ES); Jesus Garcia, Barcelona (ES); Pere Tarin, Sabadell (ES); Rosa Arola, Barcelona (ES); Montserrat Rutllan, Barcelona (ES); Amadeo Perez, Barcelona (ES)

(73) Assignee: Pierre Fabre Medicament, Boulogne-Billancourt (FR)

( * ) Notice: Subject to any disclaimer, the term of this patent is extended or adjusted under 35 U.S.C. 154(b) by 1598 days.

(21) Appl. No.: 10/492,417

(22) PCT Filed: Oct. 10, 2002

(86) PCT No.: PCT/FR02/03447

§ 371 (c)(1),
(2), (4) Date: Sep. 20, 2004

(87) PCT Pub. No.: WO03/030870

PCT Pub. Date: Apr. 17, 2003

(65) Prior Publication Data
US 2006/0110460 A1 May 25, 2006

(30) Foreign Application Priority Data
Oct. 10, 2001 (ES) .................................. 0102261
Oct. 10, 2001 (FR) .................................. 01 13031

(51) Int. Cl.
*A61K 9/14* (2006.01)
*A61K 9/16* (2006.01)
(52) U.S. Cl. .................... 424/490; 424/489; 424/491
(58) Field of Classification Search ................ None
See application file for complete search history.

(56) References Cited

U.S. PATENT DOCUMENTS

| 3,523,906 A | 8/1970 | Vrancken et al. |
| 5,733,567 A | 3/1998 | Arola et al. |

FOREIGN PATENT DOCUMENTS

| EP | 0 469 520 A2 | 2/1992 |
| EP | 0 582 459 A2 | 2/1994 |
| EP | 1 048 301 A1 | 11/2000 |
| JP | A 07-196479 | 8/1995 |
| WO | WO 95/28149 | 10/1995 |
| WO | WO 0062761 | * 10/2000 |

OTHER PUBLICATIONS

H. Okada, "One- and three-month release injectable microspheres of the LH-RH superagonist leuprorelin acetate", Advanced Drug Delivery Reviews, 28 (1997), pp. 43-70.
Uchida, et al. "Optimization of Preparative Conditions for Polylactide (PLA) Microspheres Containing Ovalbumin", *Chem. Pharm. Bull.* 43(9) 1569-1573 (1995).

* cited by examiner

*Primary Examiner*—S. Tran
(74) *Attorney, Agent, or Firm*—Buchanan, Ingersoll & Rooney P.C.

(57) ABSTRACT

The invention concerns a method for preparing a pharmaceutical composition in the form of microspheres with prolonged release of a water-soluble active principle. The invention is characterized in that it comprises the following successive steps: dissolving an active principle in an appropriate amount of water; emulsifying the resulting aqueous solution of active principle with a d,l-lactide-co-glycolide matrix copolymer, of average molecular weight ranging between 40000 and 80000, dissolved in a chlorinated hydrocarbon, resulting in a first microfine and homogeneous emulsion; emulsifying said resulting first emulsion in an external aqueous phase, containing a surfactant, a viscosity-enhancing agent and an osmotic agent; extraction-evaporation of the solvent to obtain microspheres which are recuperated after filtering, washing and drying. The invention also concerns microspheres obtainable by implementing said method, having continuous release over a period of more than two months, advantageously over a period of at least three months.

24 Claims, 2 Drawing Sheets

PROLONGED RELEASE BIODEGRADABLE MICROSPHERES AND METHOD FOR PREPARING SAME

The present invention relates to a method for preparing a pharmaceutical composition in the form of microspheres with prolonged release of a water-soluble active principle. The invention also relates to microspheres which can be obtained using this method, and which exhibit continuous release of active principle over a period of more than two months, advantageously of at least three months.

Many pharmaceutical compositions, in the form of biodegradable polymer- and copolymer-based microspheres, containing pharmacologically active compounds and designed for controlled and prolonged release of said compounds, have been described in various documents of the prior state of the art. Such pharmaceutical compositions have great value for the treatment of various diseases requiring continuous and prolonged release of active principle.

However, the formulations developed to date for setting up this type of composition have various disadvantages and few of them reach the stage of clinical trials.

One of the major problems associated with these prolonged release formulations is the release of a large amount of active principle during the first hours following administration of the pharmaceutical composition. "Burst" effect or "burst" release are terms commonly used in reference to such a release. This release generally results in an abrupt increase in plasma concentrations of the medicinal product, which, in many cases, results in toxicological problems which are unacceptable for humans. This "burst" release also results in a decrease in the duration of activity of the pharmaceutical composition due to the abrupt and rapid release of a large amount of said active principle subsequent to the administration of the composition.

A second problem lies in the fact that relatively inefficient encapsulation rates are generally obtained using the conventional methods of microencapsulation, in particular when the active principle is a water-soluble medicinal product.

A third problem which must be solved in developing these formulations is the instability of the active principles in the face of the rigorous conditions used in producing the microspheres, such as high temperatures or prolonged contact of the active principle with organic solvents during the solvent evaporation step.

Several trials have been carried out in order to solve these various problems. Thus, additives such as sugars, oils, wax, proteins, polymers, salts or acids have been used in the preparation of pharmaceutical compositions in the form of microspheres. These additives, which act as substances for retaining the medicinal product in the microsphere, make it possible to increase the efficiency of the method of microencapsulation and even, possibly, to protect the active principle during the process, by playing the role of stabilizing agents.

However, the inclusion of these additives in the microspheres can lead to problems of interaction between the additives and the active principle or the polymer-based matrix, thus inducing problems in terms of toxicology and of pharmacological activity of the medicinal product. In addition, the additives, which retain the active principle inside the microspheres during the production process, have an influence on the release profile of the active principle contained in the microspheres, possibly preventing continuous release of said active principle subsequent to administration of the microspheres.

Other methods of microencapsulation have also been developed in an attempt to increase the efficiency of microencapsulation of the active principle within the microspheres, based on the use of mixtures of organic solvents, but such methods lead to problems of stability of the active principle during the microsphere production process.

Consequently, there was a need to develop a method for preparing a pharmaceutical composition in the form of biodegradable polymer- and copolymer-based microspheres designed for prolonged release of a water-soluble active principle, which does not have the disadvantages of the compositions described in the documents of the prior state of the art or of the compositions developed to date.

The present invention satisfies this need. The applicant has thus discovered, surprisingly, that the development of microspheres based on active principle and on biodegradable d,l-lactide-co-glycolide matrix copolymer having a specific molecular weight and a specific lactic acid/glycolic acid ratio, using a rapid multiple emulsion/solvent evaporation method, without using any additive or a modulating agent as is the case in patent FR 2 718 642, makes it possible to obtain microspheres exhibiting continuous and sustained release of active principle over a period of more than two months, while at the same time exhibiting a limited "burst" effect. Such a method of encapsulation, which uses conditions which are gentle and relatively nonaggressive for the medicinal product, also makes it possible to preserve the stability of said medicinal product and to obtain a homogeneous distribution of the medicinal product within the microsphere obtained.

The physical principle of multiple emulsion for encapsulating water-soluble active principles has in particular been described in U.S. Pat. No. 3,523,906. In general, in a method of this type by W/O/W multiple emulsion and solvent evaporation, the water-soluble active principle is first of all solubilized in the internal phase of a first W/O emulsion, and then, secondly, this first emulsion is in turn emulsified in an external aqueous phase.

The applicant has discovered, surprisingly, that the use of an osmotic agent during the step for emulsifying the first emulsion in the external aqueous phase makes it possible to obtain a particularly high encapsulation efficiency by increasing the content of active principle encapsulated within the polymer matrix, and to influence the size of the microspheres.

The subject of the present invention, relating to a rapid, very efficient method of encapsulation which is relatively nonaggressive for the active principle, thus makes it possible to obtain microspheres, based on water-soluble active principle and on d,l-lactide-co-glycolide matrix copolymer, exhibiting continuous and sustained release of active principle over a period of more than two months, preferably of at least three months, while at the same time exhibiting a small "burst" effect during the hours following administration of the composition.

A subject of the present invention is thus a method for preparing a pharmaceutical composition in the form of microspheres with prolonged release of a water-soluble active principle, characterized in that it comprises the succession of steps below:

dissolving the active principle in an appropriate amount of water, emulsifying the aqueous solution of active principle thus obtained with a solution of a d,l-lactide-co-glycolide matrix copolymer of average molecular weight of between 40 000 and 80 000 and having a lactic acid/glycolic acid proportion of between 50/50 and 80/20, dissolved in a chlorinated hydrocarbon, resulting in a first microfine and homogeneous emulsion, the size of said emulsion being advantageously less than 1 μm, emulsifying said first emulsion thus obtained, in an external aqueous phase containing a surfactant, a viscosity-increasing agent and an osmotic agent, extracting-evaporating the solvent so as to obtain microspheres, which are recovered after filtration, washing and drying.

Other characteristics and advantages will emerge on reading the detailed description given below, in particular based on some examples of particular implementations.

The water-soluble active principle which can be used in the context of the method according to the present invention is advantageously chosen from the group consisting of peptides, proteins, vaccines, antibiotics, antidepressants, analgesics, anti-inflammatories and cytostatics. Even more advantageously according to the present invention, the active principle is 5-OxoPro-His-Trp-Ser-Tyr-D-Leu-Leu-Arg-ProN-HEt or one of its salts. This active principle is a GnRH hormone analogue with agonist activity.

In the context of the method according to the present invention, the first step for dissolving the active principle in water so as to form an internal aqueous phase is carried out without the addition of any substance which retains the active principle, nor of agent for stabilizing the emulsion, and without any operation intended to increase the viscosity. Advantageously according to the present invention, the active principle is dissolved in the internal aqueous phase without any additive or adjuvant.

The concentrations used in the internal aqueous phase in the context of the present invention depend on the water-solubility of the active principle, on the characteristics of said active principle and on the desired duration of release to be obtained. Advantageously according to the present invention, the active principle is present at a concentration of between 0.01 and 95% by weight, advantageously between 0.5 and 40% by weight, relative to the total weight of the internal aqueous phase.

The first emulsion can in particular be formed using an ultrasound device or a homogenizer.

The matrix copolymer which can be used, according to the present invention, for preparing microspheres by W/O/W must be able to be solubilized in an appropriate volatile solvent, such as halogenated alkanes. Advantageously according to the present invention, the solvent is a chlorinated hydrocarbon such as methylene chloride, chloroform, chloroethane, dichloroethane or trichloroethane. Even more advantageously according to the present invention, the chlorinated hydrocarbon is methylene chloride.

The d,l-lactide-co-glycolide matrix copolymer which can be used in the method according to the present invention has the cumulative advantages of being water-insoluble, of being biodegradable (such a copolymer is absorbed without accumulating in the vital organs and is, finally, completely eliminated), of being biocompatible with the organism and of being perfectly tolerated by it, and, finally, of having a minimal inflammatory response.

In the context of the method according to the present invention, the solution of the d,l-lactide-co-glycolide matrix copolymer is obtained by dissolving the copolymer in a chlorinated hydrocarbon such as methylene chloride, without the addition of any release-modulating agent. In fact, it has been discovered that the use of a release-modulating agent is not suitable for the production of microspheres designed for release over a period of time of more than two months.

The selection made with respect to the copolymer, with a specific molecular weight and a specific lactic acid/glycolic acid ratio, combined with the fact of not using a release-modulating agent in the method which is the subject of the present invention thus provides the advantage of obtaining microspheres exhibiting continuous and sustained release of active principle over a period of more than two months, preferably of at least three months, while at the same time exhibiting a limited "burst" effect during the hours following administration of the composition.

The concentrations of the polymer dissolved in the organic solution of methylene chloride depend on the active principle and on the desired rate of release. Advantageously according to the method which is the subject of the present invention, the matrix copolymer is present at a concentration of between 5 and 50% by weight relative to the total weight of the solution consisting of the copolymer dissolved in the chlorinated hydrocarbon.

According to the method which is the subject of the present invention, the external aqueous phase contains a surfactant such as polysorbate 80, a viscosity-increasing agent such as polyvinylpyrrolidone and an osmotic agent such as mannitol or sodium chloride. Advantageously according to the present invention, the external aqueous phase contains a solution of polysorbate 80, of polyvinylpyrrolidone and of mannitol or of sodium chloride. Even more advantageously according to the present invention, the external aqueous phase contains a solution of polysorbate 80, of polyvinylpyrrolidone and of sodium chloride.

Advantageously according to the method which is the subject of the present invention, the surfactant is present at a concentration of between 0.1 and 0.5% by weight, the viscosity-increasing agent is present at a concentration of between 1 and 25% by weight and the osmotic agent is present at a concentration of between 0.1 and 10% by weight, relative to the total weight of the external aqueous phase. The composition of the external aqueous phase is determinant for the formation of the second emulsion (emulsification of the first emulsion), and it is, consequently, determinant for the production of the microspheres. It thus contributes to the rapid stabilization of the microspheres, it influences the efficiency of encapsulation of the active principles, and it constitutes an essential factor for controlling the size of the final microspheres and their morphology.

During the step consisting of extraction-evaporation of the solvent, the solvent is rapidly eliminated at ambient temperature and under atmospheric pressure, according to a continuous evaporating system consisting of a slope of adequate length, over which the suspension of microspheres flows in a thin layer.

Such a system for continuous evaporation of the organic solvent, which increases and promotes contact between the emulsion and the air, makes it possible to obtain rapid stabilization of the polymer matrix, the effect of which is to increase the stabilization of the active principle while at the same time trapping a high percentage of said principle within the microspheres (efficiency of encapsulation), and to produce rapid evaporation of the solvent, the effect of which is to reduce the total time for implementation of the method. The rapid stabilization of the polymer matrix obtained during this step for extraction-evaporation of the organic solvent also makes it possible to obtain a homogeneous distribution of the active substance throughout the microsphere (thus making it possible to obtain a low concentration of active principle encapsulated close to the surface of the microsphere), thus contributing to decreasing the phenomenon of "burst" release, subsequent to administration of the microspheres. In addition, implementing the method at ambient temperature and under atmospheric pressure makes it possible to avoid problems such as alteration of thermolabile products or rupture of the microspheres when a vacuum is used during the extraction-evaporation step.

In a more detailed manner, the method for producing the microspheres according to the present invention comprises the following steps:

A certain amount of active principle is dissolved in a volume of water. This solution is emulsified, using an ultrasound device for example, in a volume of methylene chloride containing a poly(lactide-co-glycolide) copolymer of average molecular weight of between 40 000 and 80 000 daltons and having a proportion of lactic acid to glycolic acid of between 50/50 and 80/20. The first emulsion which results therefrom should be microfine and homogeneous, thus making it possible to spread the active principle throughout the polymer matrix, ensuring reproducibility of the various batches, without needing to use surfactants or other adjuvants. Once the first emulsion is formed, it is in turn emulsified in an external phase, consisting of an aqueous solution of polysorbate 80 as surfactant, of polyvinylpyrrolidone as viscosity-increasing agent and of mannitol or NaCl as osmotic agent, with stirring for a short period of time. After this step, the double emulsion is diluted with water, and the suspension is then passed, under atmospheric conditions, over a continuous evaporating system consisting of a slope of adequate length, over which the suspension of microspheres flows in a thin layer. This system makes it possible to promote contact between the emulsion and the atmosphere, which reduces the amount of time for evaporation of the organic solvent, and to increase the stabilization of the active principle. The microspheres obtained in this way are then recovered by filtration, washed with water, and dried by lyophilization.

The microspheres obtained according to the method which is the subject of the present invention are microspheres with a high content of active principle, allowing continuous release in vivo of the medicinal product over a period of more than two months, preferably of at least three months, with a small "burst" effect, after parenteral administration of the microspheres.

A subject of the present invention is also the microspheres which can be obtained by implementing the method according to the present invention, exhibiting continuous release of active principle over a period of more than two months, advantageously over a period of at least three months.

Advantageously according to the present invention, the active principle is present at a concentration of between 0.5 and 20% by weight, advantageously between 5 and 15% by weight, relative to the total weight of the microspheres.

Advantageously according to the present invention, the microspheres are less than 250 µm, even more advantageously less than 90 µm, in size. This size is suitable for administration of the microspheres.

The microspheres according to the present invention are advantageously administered parenterally, even more advantageously in the form of intramuscular, subcutaneous or intra-arterial injections, or injections at the site of a tumor. For suitable administration, the microspheres are preferably dispersed in a standard aqueous medium with dispersing agents and isotonic agents.

The following examples (studies in vivo and in vitro) are given in a nonlimiting capacity and illustrate the present invention.

EXAMPLE 1 (COMPARATIVE)

Batches of microspheres based on 5-OxoPro-His-Trp-Ser-Tyr-D-Leu-Leu-Arg-ProNHEt acetate are prepared in accordance with the method of production described in the publication *Advanced Drug Delivery Reviews,* 2.8 (1997), 43-70, which differs from the method which is the subject of the present invention. The microspheres are produced by dissolving an appropriate amount of active principle in water, and then by emulsifying the aqueous solution of active principle thus obtained, with a solution of a polylactide (100% lactide) of average molecular weight 15 000, in methylene chloride. The emulsification is carried out with a stirrer, with vigorous stirring. Once the first $W_1/O$ emulsion has been formed, it is in turn emulsified, in order to obtain a $W_1/O/W_2$ emulsion, with an aqueous solution of polyvinyl alcohol (0.25%) using a high speed mixer. The double emulsion which results therefrom is then stirred gently for several hours in order to evaporate the organic solvent. The microspheres are then washed, recovered by centrifugation and lyophilized. The final load of the microspheres with medicinal product is 9 to 11% by weight.

The main differences between the microspheres obtained according to the method described in the document of the prior art mentioned above and those obtained according to the method which is the subject of the present invention lie in:

the choice of the polymer. In example 1, the polymer used is a polylactide (100% lactide) of average molecular weight 15 000. It is a standard polymer, according to that document, for prolonged release of 5-OxoPro-His-Trp-Ser-Tyr-D-Leu-Leu-Arg-ProNHEt acetate over a period of three months;

the composition of the aqueous external phase, which consists of a polyvinyl alcohol (0.25%) in example 1;

the system for evaporating the organic solvent. In example 1, the double emulsion is stirred for several hours.

EXAMPLE 2

According to the method of production which is the subject of the present invention, the 5-OxoPro-His-Trp-Ser-Tyr-D-Leu-Leu-Arg-ProNHEt acetate is dissolved in water, and the aqueous solution of active principle is then emulsified, using an ultrasound device, in a solution of methylene chloride containing 15% of a d,l-lactide-co-glycolide copolymer, this copolymer having an average molecular weight of 63 000 daltons (inherent viscosity of approximately 0.6 dl/g) and a proportion of lactic acid to glycolic acid of 75/25. Once the first emulsion has been formed, it is in turn emulsified with an aqueous solution consisting of 0.25% of polysorbate 80, 7% of polyvinylpyrrolidone and 5% of mannitol, with stirring, using a propeller blade stirrer. After this step, the double emulsion is passed, under atmospheric conditions, over a continuous evaporating system consisting of a slope of adequate length, over which the suspension of microspheres flows in a thin layer. Using such an evaporating system, the organic solvent is rapidly evaporated, resulting in rapid stabilization of the polymer matrix. The microspheres are finally recovered by filtration, washed with water, and then dried under lyophilization. The final load of medicinal product in the microspheres is 9 to 11% by weight.

EXAMPLE 2a

Microspheres are produced according to the method described in example 2, using 5% of sodium chloride in the external aqueous phase as osmotic agent, instead of 5% of mannitol.

EXAMPLE 3

The in vitro release of 5-OxoPro-His-Trp-Ser-Tyr-D-Leu-Leu-Arg-ProNHEt acetate from the microspheres prepared according to examples 1 and 2 is studied in a phosphate buffer.

25 mg of each formulation in the form of microspheres are suspended in a release medium made up of 5 ml of phosphate buffer (pH=7.4), and then stirred (rotation) for 4 days at 37° C. At various times, the amount of peptide released was measured by high pressure liquid chromatography (HPLC).

The results of this study are given in table 1. They demonstrate that the composition prepared in accordance with the method which is the subject of the present invention (example 2) exhibits a "burst" release which is much less than the "burst" release of the compositions prepared in accordance with the method of the prior art of example 1. Thus, 4 days after the beginning of the study, the microspheres of example 2 have released only 3.4% of the total amount of peptide present in the microspheres, whereas the microspheres of example 1 have released up to 22.6% thereof.

TABLE 1

| | % of peptide released | |
|---|---|---|
| Time | Example 1 | Example 2 |
| 1 day | 13.4% | 1.0% |
| 2 days | 16.7% | 1.4% |
| 4 days | 22.6% | 3.4% |

EXAMPLE 4

The in vivo release of 5-OxoPro-His-Trp-Ser-Tyr-D-Leu-Leu-Arg-ProNHEt acetate from the microspheres prepared according to example 1, 2 and 2a is studied in rats.

For this study, the three type of microspheres (examples 1, 2 and 2a) are suspended in a standard aqueous excipient, before being administered to rats subcutaneously at a dorsal region shaved beforehand. The dose administered to each animal is 3.6 mg of microencapsulated 5-OxoPro-His-Trp-Ser-Tyr-D-Leu-Leu-Arg-ProNHEt acetate. Some rats are sacrificed three days after administration, whereas others are sacrificed seven days after administration. Once the rats are dead, the site of injection is then excised, and the microspheres remaining at the site of injection, along with the contiguous connective tissue, are then recovered. The 5-Oxo-Pro-His-Trp-Ser-Tyr-D-Leu-Leu-Arg-ProNHEt acetate remaining is then extracted, and then quantified by high pressure liquid chromatography (HPLC).

The results of this study are given in table 2. It can be seen that, after 3 days, the microspheres of example 1 have already released 35.3% of the total amount of peptide present in the microspheres, whereas the microspheres of example 2 have released only 20.6%.

TABLE 2

| | % of peptide released | | |
|---|---|---|---|
| Time | Example 1 | Example 2 | Example 2a |
| 3 days | 35.3% | 20.6% | 25.9% |
| 7 days | 41.6% | 29.5% | — |

It may thus be concluded that the results of this in vivo study are in agreement with the results obtained in vitro (example 3) and demonstrate that the formulations prepared in accordance with the method of the present invention exhibit a "burst" release which is much less substantial than the "burst" release of the compositions prepared in accordance with the method of the prior art of example 1.

EXAMPLE 5

In order to complete the preceding results (examples 3 and 4), a thorough study of the in vivo release of active principle during the first 24 hours following administration of the microspheres was carried out.

In this trial, the serum content of 5-OxoPro-His-Trp-Ser-Tyr-D-Leu-Leu-Arg-ProNHEt acetate is evaluated in rats by liquid chromatography-mass spectrometry-mass spectrometry (LC/MS/MS), after subcutaneous administration of the formulations in the form of microspheres prepared according to examples 1 and 2. Thus, 3.6 mg of encapsulated 5-OxoPro-His-Trp-Ser-Tyr-D-Leu-Leu-Arg-ProNHEt acetate are injected into rats and, at various times after administration, blood samples are taken in order to estimate the content of 5-OxoPro-His-Trp-Ser-Tyr-D-Leu-Leu-Arg-ProNHEt acetate in the serum.

Figure 1:
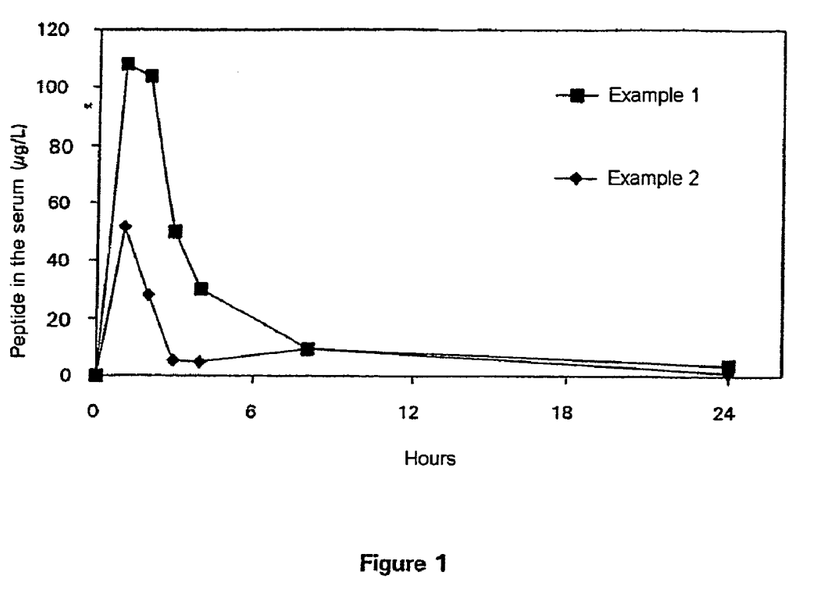
FIG. 1 is a graph comparing the results obtained for products of Example 1 (comparative) and Example 2 (invention) in terms of the amount of peptide in the serum (µg/L) at various time points over a 24-hour period.

The results of this study are given in FIG. 1. Thus, one hour after administration of the microspheres of example 1, the concentration of peptide in the serum is 107.8 µg/l, whereas, for the microspheres of example 2, the concentration of peptide in the serum is 51.8 µg/l. After 2, 3, 4, 8 and 24 hours, the microspheres of example 1 exhibit, respectively, serum concentrations of 103.7, 50.1, 30.3, 9.5 and 3.8 µg/l, whereas the microspheres of example 2 exhibit, respectively, values of 28.0, 5.5, 4.5, 9.3 and 1.0 µg/l.

Thus, the results of this study are in agreement with the results obtained for examples 3 and 4, since it is noted that the microspheres of example 2 release less peptide during the first 24 hours ("burst" effect) than the microspheres of example 1. It may be concluded that, when the microspheres contain the polymer matrix according to the present invention, and when they are produced using the method according to the present invention, they exhibit a "burst" release which is substantially less than with the microspheres prepared in accordance with the method of the prior art, after in vivo administration.

EXAMPLE 6

The complete profile for release of 5-OxoPro-His-Trp-Ser-Tyr-D-Leu-Leu-Arg-ProNHEt acetate from the microspheres prepared according to example 2 is studied in rats. The aim of the study is to demonstrate that, subsequent to the phenomenon of "burst" release (which occurs systematically, but which is relatively low compared to microspheres described in the prior art), the microspheres obtained according to the method of the present invention release the peptide continuously over a period of several months.

In a manner similar to example 4, the microspheres are suspended in a standard aqueous vehicle so that they can be administered to rats subcutaneously at a dorsal region which has been shaved beforehand. The dose administered to each animal is 3.6 mg of encapsulated 5-OxoPro-His-Trp-Ser-Tyr-D-Leu-Leu-Arg-ProNHEt acetate.

At various times over a period of three months, groups of rats are sacrificed, the site of injection is excised, and the microspheres remaining at the site, along with the contiguous connective tissue, are then recovered. The 5-OxoPro-His-Trp-Ser-Tyr-D-Leu-Leu-Arg-ProNHEt acetate remaining at the site of injection is then extracted, and then quantified by high pressure liquid chromatography (HPLC).

Figure 2:
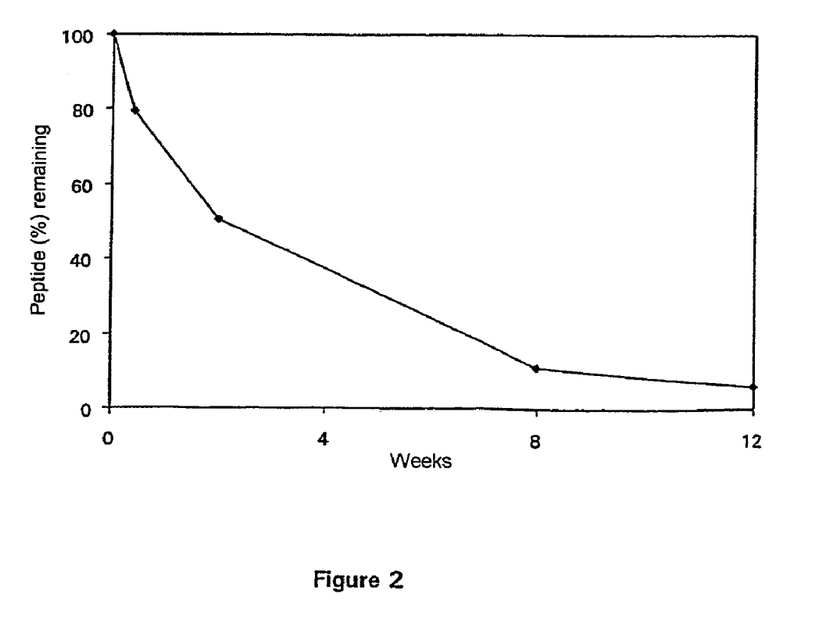
FIG. 2 is a graph illustrating the percentage amount of peptide remaining at various time points over a 12-week period for a product prepared in accord with the invention in Example 2, when tested as described in Example 6.

The results of this study are given in FIG. 2. They thus show that the microspheres release the peptide continuously over a period of at least three months.

EXAMPLE 7

The in vivo biological activity of the 5-OxoPro-His-Trp-Ser-Tyr-D-Leu-Leu-Arg-ProNHEt acetate micro-encapsulated in microspheres prepared according to example 2 and example 2a is studied here.

5-OxoPro-His-Trp-Ser-Tyr-D-Leu-Leu-Arg-ProNHEt acetate is an analogue which is a powerful LH-RH hormone agonist and which stimulates gonadotrophin secretion by the pituitary gland and steroidogenesis in the genital organs at acute doses. However, when it is administered chronically, it produces, paradoxically, agonistic inhibitory effects on pituitary gland gonadotrophin and testicular and ovarian steroidogenesis. Initial administration of 5-OxoPro-His-Trp-Ser-Tyr-D-Leu-Leu-Arg-ProNHEt acetate causes an abrupt increase in serum levels of gonadotrophins and of sex hormones, but, in the case of continuous exposure to the medicinal product, these hormone levels decrease substantially until they reach levels below the initial base values, after several days of administration, and this phenomenon persists for the duration of the treatment.

Consequently, in order to verify that the small "burst" release of the formulations produced according to examples 2 and 2a does not alter its pharmacological activity, 3.6 mg of 5-OxoPro-His-Trp-Ser-Tyr-D-Leu-Leu-Arg-ProNHEt acetate microencapsulated in these microspheres are injected into rats subcutaneously and, at various times after administration, blood samples are taken in order to estimate the serum testosterone by radioimmunoassay.

Figure 3:
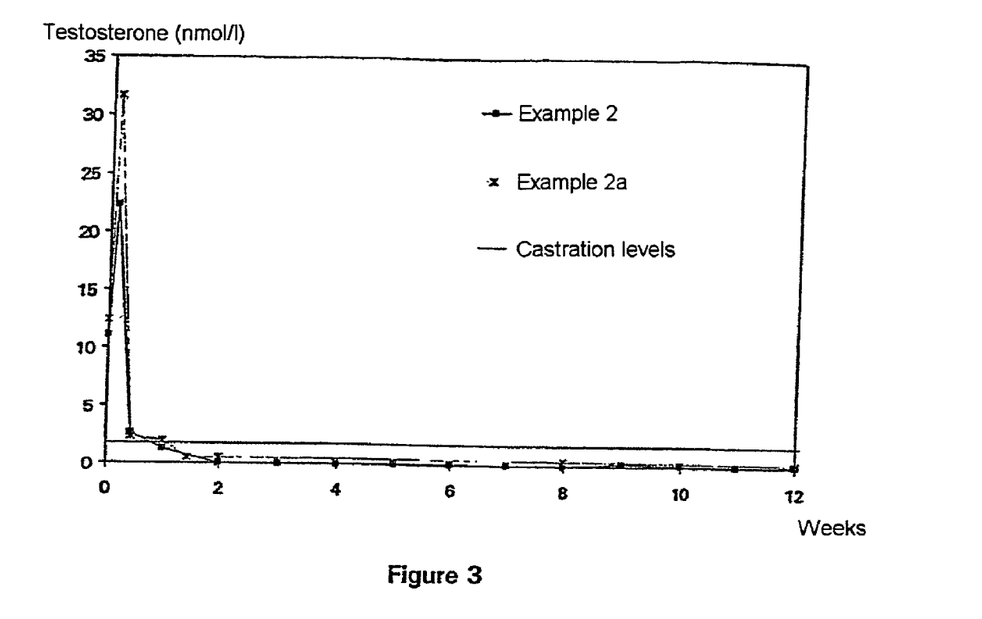
FIG. 3 is a graph illustrating the results for products of Example 2 and 2a when tested as described in Example 7.

The results of this study are given in FIG. 3. The results thus show an appropriate serum testosterone profile: an abrupt increase during the first days, followed by a suppression of the plasma testosterone concentration, and they thus demonstrate a correct biological activity of the peptide released from the formulation according to the present invention.

The object of examples 8 to 10 is to show the various advantages that the microspheres prepared in accordance with the method which is the subject of the present invention exhibit compared to the microspheres prepared according to the method described in patent FR 2 718 642. The main differences which exist between the present invention and the invention described in patent FR 2 718 642 are as follows:

No release-modulating agent used in the method of the present invention.

Addition of mannitol or of NaCl, as osmotic agent, to the external aqueous phase in which the first emulsion is emulsified.

Selection of a molecular weight range (40 000 to 80 000) and of a lactic acid/glycolic acid proportion range (50/50 to 80/20) for the d,l-lactide-co-glycolide (PLGA) copolymer in the present invention.

EXAMPLE 8

Effect of the Release-Modulating Agent on the Release In Vitro

Microspheres are prepared according to the method of production described in example 2, using, as organic phase, a solution of methylene chloride containing 30% of a d,l-lactide-co-glycolide copolymer having an average molecular weight of 34 000 daltons (inherent viscosity of approximately 0.4 dl/g) and a proportion of lactic acid to glycolic acid of 50/50, and also various amounts (examples 8.1, 8.2 and 8.3) of a poly(d,l-lactide) having an average molecular weight of 2000 daltons (PLA 2000).

EXAMPLE 8.1

0% of PLA 2000

EXAMPLE 8.2

2.5% of PLA 2000

EXAMPLE 8.3

5% of PLA 2000

The external aqueous phase is an aqueous solution made up of 0.25% of polysorbate 80, 4% of polyvinylpyrrolidone and 5% of mannitol.

The initial in vitro release of 5-OxoPro-His-Trp-Ser-Tyr-D-Leu-Leu-Arg-ProNHEt acetate from the microspheres prepared according to examples 8.1, 8.2 and 8.3 is effected in a phosphate buffer.

25 mg of each formulation are suspended in a release medium made up of 5 ml of phosphate buffer (pH=7.4), and then stirred (rotation) for 7 days at 37° C. At various times, the amount of peptide released is measured by high pressure liquid chromatography (HPLC). The results are given in table 3 below.

TABLE 3

| Time | Peptide released in % | | |
|---|---|---|---|
| Days | Example 8.1 | Example 8.2 | Example 8.3 |
| 2 days | 1.1% | 1.1% | 1.6% |
| 4 days | 1.7% | 2.7% | 2.9% |
| 7 days | 3.7% | 11.8% | 18.3% |

The results show, for these 3 cases 8.1, 8.2 and 8.3, a very small "burst" release and show that the release-modulating agent (PLA) has an effect that accelerates the release of the active principle, even at low concentrations (2.5%) of PLA, indicating that the use of this agent may not be suitable for the production of microspheres designed for prolonged release (over a period of three months).

EXAMPLE 9

Effect of the Release-Modulating Agent on the Pharmacodynamic Profile and Selection of the Polymer for a Prolonged Release Over Three Months The effect of the polymer composition of the microspheres on the release of the active principle is studied in a pharmacodynamic study carried out in rats. The microspheres are prepared according to the method of production described in example 2, using various types of polymer:

EXAMPLE 9.1

Mixture of 97.5% of a d,l-lactide-co-glycolide copolymer having an average molecular weight of 34 000 daltons and a proportion of lactic acid to glycolic acid of 50/50, and of 2.5% of a poly(d,l-lactide) having an average molecular weight of 2000 daltons (release-modulating agent).

EXAMPLE 9.2 d,l-lactide-co-glycolide copolymer having an average molecular weight of 34 000 daltons and a proportion of lactic acid to glycolic acid of 50/50.

EXAMPLE 9.3 d,l-lactide-co-glycolide copolymer having an average molecular weight of 63 000 daltons and a proportion of lactic acid to glycolic acid of 75/25.

The study of in vivo release of 5-OxoPro-His-Trp-Ser-Tyr-D-Leu-Leu-Arg-ProNHEt acetate from the microspheres is followed through its pharmacological effect of suppression of plasma testosterone levels.

Figure 4:
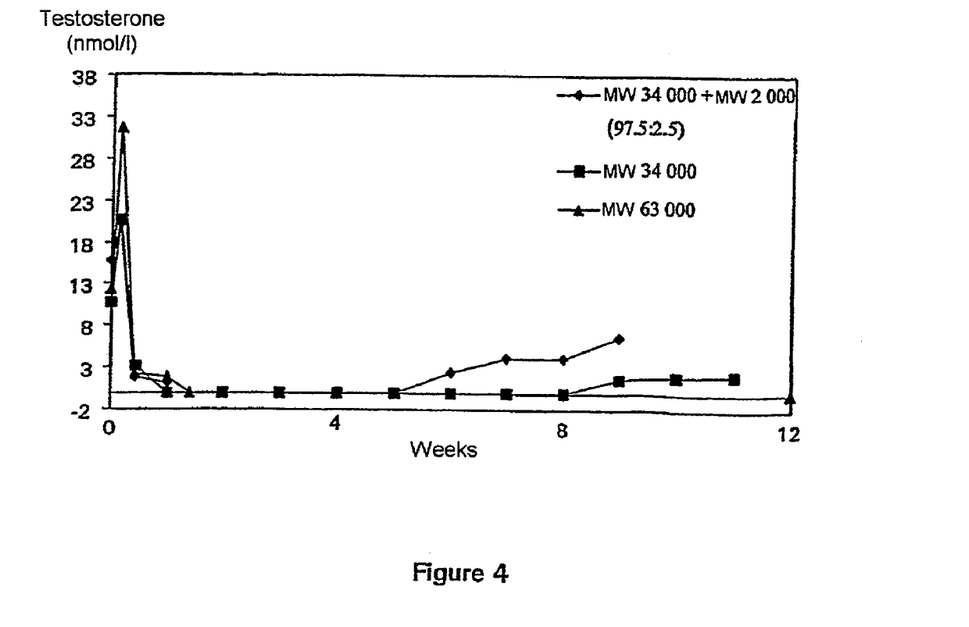
FIG. 4 is a graph showing the results of the study detailed in Example 9, where variously defined polymers are used, and also showing the effect of release modulating agent.

The results of this study are given in FIG. 4. The results thus confirm that the presence of the release-modulating agent accelerates the release of the active principle, and that the release-modulating agent cannot therefore be used in formulations with very prolonged release (testosterone levels suppressed for 5 weeks).

The results also show that a d-l-lactide-co-glycolide copolymer having an average molecular weight of 34 000 daltons and a proportion of lactic acid to glycolic acid of 50/50 can maintain the testosterone levels suppression for 8 weeks, whereas a d,l-lactide-co-glycolide copolymer having an average molecular weight of 63 000 daltons and a proportion of lactic acid to glycolic acid of 75/25 can maintain the castration for at least three months.

EXAMPLE 10

Effect of the Addition of an Osmotic Agent to the External Aqueous Phase

Formulation 10.1

Microspheres are prepared according to the method of production described in example 2, using, as external aqueous phase, a solution made up of 0.25% of polysorbate 80 and 4% of polyvinylpyrrolidone.

Formulation 10.2

Microspheres are prepared according to the method of production described in example 10.1, adding between 2.5% and 5% of mannitol to the external aqueous phase as osmotic agent.

EXAMPLE 10.3

Microspheres are prepared according to the method of production described in example 10.1, adding between 2.5% and 5% of sodium chloride to the external aqueous phase as osmotic agent.

The results of the study showing the influence of the osmotic agent in the external aqueous phase are given in table 4 below:

TABLE 4

| Example | Osmotic agent | Size μm | Content % |
| --- | --- | --- | --- |
| 10.1 | — | 59.3 | 7.7 |
| 10.2 | 2.5% mannitol | 50.4 | 10.5 |
| 10.2 | 5% mannitol | 43.8 | 10.7 |
| 10.3 | 2.5% NaCl | 39.7 | 10.7 |
| 10.3 | 5% NaCl | 32.7 | 10.4 |

Thus, the size and the peptide content of the microspheres depend on the presence of the osmotic agent in the external aqueous phase. The addition of mannitol or of NaCl as osmotic agent increases the efficiency of encapsulation, i.e. the percentage of active principle microencapsulated (content). The type and the amount of the osmotic agent added can also make it possible to control the size of the particles. In the context of the present invention, NaCl is advantageously used as osmotic agent, since it has been demonstrated that, under identical conditions for stirring and for the viscosity, sodium chloride allows a greater decrease in the size of the particles than mannitol, without however producing a decrease in the efficiency of encapsulation.

EXAMPLE 11

Effect of the Concentration of the Viscosity-Increasing Agent (Viscosity-Modifying Agent) Present in the External Aqueous Phase, on the Size of the Particles Formulation 11.1

Microspheres are prepared according to the method of production described in example 2, but without active principle, using, as external aqueous phase, a solution made up of 0.25% of polysorbate 80, 5% of mannitol and 6.8% of polyvinylpyrrolidone.

Formulation 11.2

Microspheres are prepared according to the method of production described in example 2, but without active principle, using, as external aqueous phase, a solution made up of 0.25% of polysorbate 80, 5% of mannitol and 8.0% of polyvinylpyrrolidone.

The results of the study showing the influence of the viscosity-modifying agent in the external aqueous phase are given in table 5 below.

TABLE 5

| Example | Viscosity-modifying agent | Size μm |
| --- | --- | --- |
| 11.1 | 6.8% polyvinylpyrrolidone | 31.3 |
| 11.2 | 8.0% polyvinylpyrrolidone | 25.4 |

Example 10.2, developed with an external aqueous phase made up of 0.25% of polysorbate 80, 5% of mannitol and 4% of polyvinylpyrrolidone, made it possible to obtain a particle size of 43.8 μm. By increasing the concentration of viscosity-modifying agent, it can be seen that a notable decrease in the size of the particles is obtained, as shown in table 5 above.

Thus, the size of the microspheres depends on the presence of the viscosity-modifying agent in the external aqueous phase, and on its concentration.

The invention claimed is:

1. A method for preparing a pharmaceutical composition in the form of microspheres with prolonged release of a water-soluble active principle, which comprises the succession of steps below:
dissolving the active principle in an appropriate amount of water,
emulsifying the aqueous solution of active principle thus obtained with a solution of a d,l-lactide-co-glycolide matrix copolymer of average molecular weight of between 40,000 and 80,000 and having a lactic acid/glycolic acid proportion of between 50/50 and 80/20, dissolved in a chlorinated hydrocarbon, in the absence of a release-modulating agent, resulting in a first microfine and homogeneous emulsion, wherein the d,l-lactide-co-glycolide matrix copolymer is present at a concentration of between 5 and 50% by weight relative to the total weight of the solution consisting of the copolymer dissolved in the chlorinated hydrocarbon,
emulsifying said first emulsion thus obtained, in an external aqueous phase containing a surfactant, a viscosity-increasing agent and an osmotic agent,
extracting-evaporating the solvent so as to obtain microspheres, which are recovered after filtration, washing and drying;
the resultant microspheres exhibiting continuous release of active principle over a period of time of more than two months.

2. The method as claimed in claim 1, wherein the active principle is selected from the group consisting of peptides, proteins, vaccines, antibiotics, antidepressants, analgesics, anti-inflammatories and cytostatics.

3. The method as claimed in claim 2, wherein the active principle is 5-OxoPro-His-Trp-Ser-Tyr-D-Leu-Leu-Arg-PrONHEt or one of its salts.

4. The method as claimed in claim 1, wherein the first step for dissolving the active principle in water so as to form an internal aqueous phase is carried out without the addition of any substance which retains the active principle, nor of agent for stabilizing the emulsion, and without any operation intended to increase the viscosity.

5. The method as claimed in claim 1, wherein the active principle is present at a concentration of between 0.01 and 95% by weight relative to the total weight of the internal aqueous phase.

6. The method as claimed in claim 1, wherein the chlorinated hydrocarbon is methylene chloride.

7. The method as claimed in claim 1, wherein the external aqueous phase contains a solution of polysorbate 80, of polyvinylpyrrolidone and of mannitol or of sodium chloride.

8. The method as claimed in claim 1, wherein the surfactant is present at a concentration of between 0.1 and 0.5% by weight, the viscosity-increasing agent is present at a concentration of between 1 and 25% by weight and the osmotic agent is present at a concentration of between 0.1 and 10% by weight, relative to the total weight of the external aqueous phase.

9. The method as claimed in claim 1, wherein, during the step comprising extraction-evaporation of the solvent, the solvent is rapidly eliminated at ambient temperature and under atmospheric pressure, according to a continuous evaporating system comprising a slope of adequate length, over which the suspension of microspheres flows in a thin layer.

10. The method as claimed in claim 1, wherein the resultant microspheres are less than 250 μm in size.

11. The method as claimed in claim 1, wherein the resultant microspheres are less than 90 μm in size.

12. The method as claimed in claim 5, wherein the active principle is present at a concentration of between 0.5 and 40% by weight relative to the total weight of the internal aqueous phase.

13. A method for preparing a pharmaceutical composition in the form of microspheres with prolonged release of a water-soluble active principle, which comprises the succession of steps below:
dissolving the active principle in an appropriate amount of water,
emulsifying the aqueous solution of active principle thus obtained with a solution of a d,l-lactide-co-glycolide matrix copolymer of average molecular weight of between 40,000 and 80,000 and having a lactic acid/glycolic acid proportion of between 50/50 and 80/20, dissolved in a chlorinated hydrocarbon, in the absence of a release-modulating agent, resulting in a first microfine and homogeneous emulsion, wherein the d,l-lactide-co-glycolide matrix copolymer is present at a concentration of between 5 and 50% by weight relative to the total weight of the solution consisting of the copolymer dissolved in the chlorinated hydrocarbon,
emulsifying said first emulsion thus obtained, in an external aqueous phase containing a surfactant, a viscosity-increasing agent and an osmotic agent,
extracting-evaporating the solvent so as to obtain microspheres, which are recovered after filtration, washing and drying;
the resultant microspheres exhibiting continuous release of active principle over a period of time of at least three months.

14. The method as claimed in claim 13, wherein the active principle is selected from the group consisting of peptides, proteins, vaccines, antibiotics, antidepressants, analgesics, anti-inflammatories and cytostatics.

15. The method as claimed in claim 14, wherein the active principle is 5-OxoPro-His-Trp-Ser-Tyr-D-Leu-Leu-Arg-ProNHEt or one of its salts.

16. The method as claimed in claim 13, wherein the first step for dissolving the active principle in water so as to form an internal aqueous phase is carried out without the addition of any substance which retains the active principle, nor of agent for stabilizing the emulsion, and without any operation intended to increase the viscosity.

17. The method as claimed in claim 13, wherein the active principle is present at a concentration of between 0.01 and 95% by weight relative to the total weight of the internal aqueous phase.

18. The method as claimed in claim 13, wherein the chlorinated hydrocarbon is methylene chloride.

19. The method as claimed in claim 13, wherein the external aqueous phase contains a solution of polysorbate 80, of polyvinylpyrrolidone and of mannitol or of sodium chloride.

20. The method as claimed in claim 13, wherein the surfactant is present at a concentration of between 0.1 and 0.5% by weight, the viscosity-increasing agent is present at a concentration of between 1 and 25% by weight and the osmotic agent is present at a concentration of between 0.1 and 10% by weight, relative to the total weight of the external aqueous phase.

21. The method as claimed in claim 13, wherein, during the step comprising extraction-evaporation of the solvent, the solvent is rapidly eliminated at ambient temperature and under atmospheric pressure, according to a continuous evaporating system comprising a slope of adequate length, over which the suspension of microspheres flows in a thin layer.

22. The method as claimed in claim 13, wherein the resultant microspheres are less than 250 μm in size.

23. The method as claimed in claim 13, wherein the resultant microspheres are less than 90 μm in size.

24. The method as claimed in claim 17, wherein the active principle is present at a concentration of between 0.5 and 40% by weight relative to the total weight of the internal aqueous phase.

* * * * *